United States Patent [19]
Wikström

[11] Patent Number: 5,912,329
[45] Date of Patent: Jun. 15, 1999

[54] METHOD FOR PURIFICATION OF A MIXTURE OF HYDROXAMATE DERIVATIZED PROTEIN AND NATIVE PROTEIN

[75] Inventor: Per Wikström, Upplands Väsby, Sweden

[73] Assignee: Chiron Corporation, Emeryville, Calif.

[21] Appl. No.: 08/635,908

[22] PCT Filed: Nov. 17, 1994

[86] PCT No.: PCT/SE94/01088

§ 371 Date: Apr. 25, 1996

§ 102(e) Date: Apr. 25, 1996

[87] PCT Pub. No.: WO95/14035

PCT Pub. Date: May 26, 1995

[30] Foreign Application Priority Data

Nov. 18, 1993 [SE] Sweden ................................ 9303822

[51] Int. Cl.$^6$ .............................. C07K 7/10; C07K 1/14; C07K 3/20
[52] U.S. Cl. .................... 530/415; 530/399; 530/416; 530/417
[58] Field of Search ................... 530/399, 415, 530/416, 417

[56] References Cited

FOREIGN PATENT DOCUMENTS

| 0 184 355 A2 | 6/1986 | European Pat. Off. . |
| 0 253 303 A2 | 1/1988 | European Pat. Off. . |
| 0167502 | 1/1996 | European Pat. Off. . |
| WO 90/12803 | 11/1990 | WIPO . |

OTHER PUBLICATIONS

Ramadan, N., Porath, J. Iron(3+)–hydroxamate as immobilized metal affinity–adsorbent for protein chromatography. J. Chromatogr., 321(1), 93–104, Jan. 1995.

Porath, J. IMAC–immobilized metal ion affinity based chromatography. Trends in analytical chemistry, 7, 254–259, Jul. 1988.

Farkas et al Complexes of peptide hydroxamates. Complex formation between transition metals and L–proplyl–L–leucylglycinehydroxamic acid [N–hydroxy–7–methyl–4–oxo–5–(pyrrolidine–2'–carboxamido)–3–azaoctanamide] and L–prolyl–L–leucinehy, Mar. 1990.

*Primary Examiner*—Cecilia J. Tsang
*Assistant Examiner*—Michael Borin
*Attorney, Agent, or Firm*—Pollock, Vande Sande & Amernick; Robert P. Blackburn

[57] ABSTRACT

The invention relates to a method for purification of a mixture of hydroxamate derivatized protein/proteins and native protein which is characterized by treating the mixture with immobilized metal and thereby adsorbing the hydroxamate derivatized protein/proteins on the immobilized-metal and recovering the native protein. The protein could be IGF-L. It also relates to a process for the production of a native protein which is characterized by expression of the protein as a fusion protein, cleavage of the fusion protein by hydroxylanine, separation of native protein from hydroxamate derivatized protein by adsorbing the hydroxamate derivatized protein on immobilized metal and directly recovering the native protein. The use of immobilized metal affinity chromatography for separation of native protein from hydroxamate derivatized protein is also claimed.

15 Claims, 2 Drawing Sheets

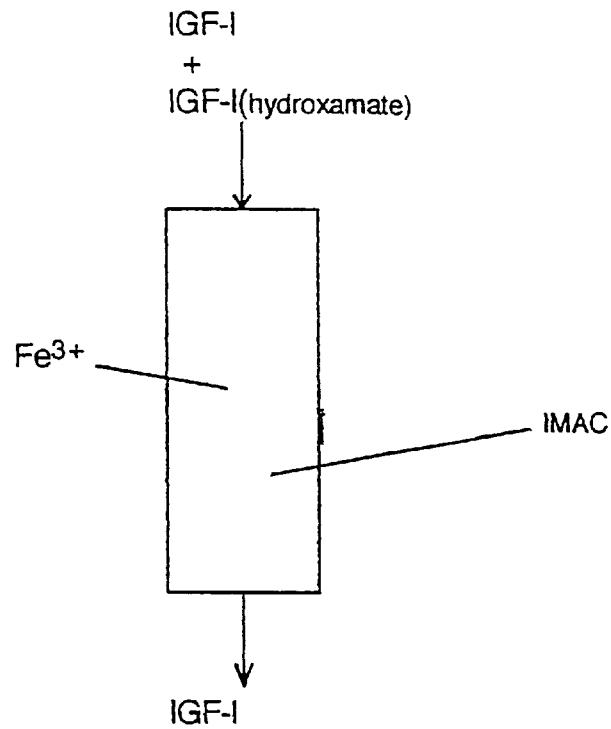
Fig 2a
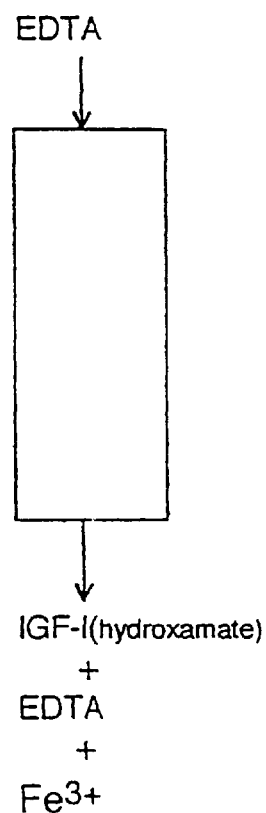
Fig 2b
Figure 2

METHOD FOR PURIFICATION OF A MIXTURE OF HYDROXAMATE DERIVATIZED PROTEIN AND NATIVE PROTEIN

The invention relates to a method for purification of a mixture of hydroxamate derivatized protein and native protein by treating the mixture with immobilized metal and thereby adsorb the hydroxamate derivatized protein on the immobilized metal and recover the native protein. The protein is e.g. IGF-I.

INTRODUCTION

One main problem when proteins are produced in expression system is related to the folding of the protein to its native configuration. Many expression systems lead to the production of aggregates of denatured proteins, so called inclusion bodies, of which only a part will lead to the desired native protein.

General methods to facilitate and render the refolding effective has been found. One is the use of a class of heat-shock-proteins (HSP) and the other is folding-enzymes. By using HSP, aggregation is avoided and by using the folding enzymes, the speed of refolding is accelerated.

Another suggested method for the recovering of the native protein is solubilization of the inclusion body protein with a denaturant, such as guanidine or urea and if needed a reduction of the disulphide bond. By dilution or dialysis and reoxidation, the protein can be refolded to the native protein.

U.S. Pat. No. 5,151,501 (American Cyanamid) discloses a process for solubilization and naturation of somatropins (Growth hormones) by dispersing somatropin refractile bodies in a solution containing sulfolane and thereafter dilution.

Human recombinant IGF-I has been produced as a secreted product in both *Escherichia coli* and *Saccharomyces cerevisiae*. In isolated material from both species, IGF-I is found mainly as mis-folded forms with intermolecular disulfide bonds. In addition, in vitro refolding of reduced IGF-I in the presence of oxygen, has demonstrated that native, mis-matched and aggregated IGF-I accumulate, even under dilute refolding conditions.

A promising system is expression of a hybrid-IGF-I molecule in a prokaryotic cell (*Escherichia coli*) as host organism. This system creates however other problems. Mammalian polypeptides expressed in prokaryotic cells occasionally form aggregates (inclusion bodies). Such aggregates or inclusion bodies are associated with improper formation of intermolecular bonds. The general approach that has been used for obtaining biologically active polypeptides is to treat the inclusion bodies with chaotropic agents and reducing agents—to refold the polypeptides into their native form. Successful refolding, without formation of new inclusion bodies, is generally difficult at high concentrations of the recombinant protein. The best yield is generally achieved at concentrations around 20–200 µg/mL. Refolding is therefore considered to be a very expensive production form that demands a cost intensive drug.

With *Escherichia coli* expressing the hybrid protein Z-IGF-I, very high expression levels have been achieved (6–7 g/l fermentation). Reference is here given to EP 230 869, especially the examples. The present bottleneck for this system is to remove the Z part in order to achieve native IGF-I after refolding.

When the recombinant construction Z-IGF-I is connected by the peptide bond of asparagine-glycine, the Z part can be efficiently removed to 70–80%, by treating the heterologous IGF-I with high concentrations of hydroxylamine (1–2M, pH 9.5) (Nilsson B, et al. Methods in Enzymology, vol 198, 1991). Unfortunately does IGF-I contain the amino acids Gln15, Asn 26 and Gln 40 that also have the potential to chemically react with hydroxylamine and form hydroxamate (Bornstein P and Balian G. Methods in Enzymology, 47, 132–145, 1977). That this unwanted side reaction actually occurs has been confirmed by Canova-Davis et al. ( Biochem J, 285, 207–213, 1992).

Even gentle treatment seems to produce too much of this side product. It is therefore creating a purification and separation requirement.

Theoretically seven forms of IGF-I can be formed during hydroxylamine cleavage with three different molecular weights ;Δ16, Δ32 and Δ48. Canova-Davis et al., 1992 reported three forms. Analytically it is shown by this work that it is possible to separate these three forms by a combination of reversed phase and anion exchange chromatography (PEI-Bakerbond). The separation using PEI was reproduced. It was found to be very sensitive to disturbances. A process if at all possible, based on this separation would probably provide the manufacture with a very unreliable process with a number of potential difficulties.

The use of hydroxylamine for removing a signal peptide in industrial production of a recombinant protein does thus not lead directly to the desired, native form of a protein containing asparagine or glutamine.

We have now found a new method for the purification and separation of native proteins which are present in a mixture together with chemically hydroxamate-altered forms, by using immobilized metal-affinity chromatograph (IMAC). This method gives an unexpected high yield of the native protein, which has not been possible earlier.

Immobilized metal-affinity chromatography is based on the interaction between a Lewis acid (ex. metal ion, electron-pair acceptor), and a Lewis base (N, S, O, electron-pair donator). If more than one donor atom are present in the same molecule, a very strong interaction can occur (chelation). A number of amino acids can potentially participate. Proteins bind metal ions mainly via amino acid residues which have electron donating side chains. Each electron donor have different affinity for different metal ions. Hard Lewis acids Al(III), Fe(III) and Ce(III), have a strong affinity for oxygen whereas Cu(II), Ni(II) have a strong affinity for nitrogen and sulphur. Proteins containing histidine have affinity for ex Ni(II), Cu(II), while phosphoproteins interact with Fe(III). The side chains of glutamine and asparagine contain amides. When the amides are converted to hydroxamate a bidentate chelate can be formed with for instance Fe(III) present (FIG. 1). It has also been shown in the litterature that hydroxamate can be used as a chelating ligand attached to Sepharose by Ramadan N. and Porath J. Journal of Chromatography, 321, 81–91, 93–104 and 105–113, 1985.

We thus claim a method for removing polypeptides/proteins, e.g. IGF-I with one or more of its asparagine or glutamine chemically altered to a hydroxamate form.

THE INVENTION

Our invention relates to a method for purification of a mixture of hydroxamate derivatized protein and native protein which is characterized by treating the mixture with immobilized-metal and thereby adsorbing the hydroxamate derivatized protein and recovering the native protein. The protein is e.g. IGF-I.

The metal can be chosen among the group of aluminium, iron, cerium, copper, zink, calcium or nickel and the metal is immobilized on a matrix with chelating ligands. The chelating ligands are known in the art and can e.g. be iminodiacetic acid(IDA), N,N,N'-tris(carboxymethyl)-ethylenediamine (TED), carboxymethylated aspartic acid (CM-ASP) or tetraethylene pentamine (TEPA), preferably is an iminodiacetic acid(IDA)-matrix, such as Chelating Sepharose® Fast Flow or TSK gel AF-Chelate TOYOPEARL 650 M used.

The invention also relates to a method for separation of native protein from hydroxamate derivatized protein which is characterized by adsorbing the hydroxamate derivatized protein on immobilized metal and directly recovering the native protein. The protein could e.g. be IGF-I or any other hydroxamate forming protein, able to interact with the chelating adsorbent.

Also disclosed is a process for the production of a native protein, such as IGF-I, which is characterized by expression of the protein as a fusion protein, cleavage of the fusion protein by hydroxylamine, separation of native protein from hydroxamate derivatized protein by adsorbing the hydroxamate derivatized protein on immobilized metal and directly recover the native protein. The process can be a continuous process in which the immobilized metal is packed in a column or a batch-wise process.

The hydroxylamine is normally bound to Gln and/or Asn, as in the case for IGF-I.

The invention also relates to the new use of immobilized metal affinity chromatography for separation of native protein from hydroxamate derivatized protein, preferably IGF-I.

The metal can be chosen among the group of aluminium, iron, cerium, copper, zink, calcium or nickel and preferably the metal is iron and immobilized on an iminodiacetic acid(IDA)-matrx, (e.g. Chelating Sepharose® Fast Flow or TSK gel AF-Chelate TOYOPEARL 650 M).

By "native protein" is meant an underivatized protein, and preferably a recombinant protein.

The invention is exemplified with IGF-I as protein, but also other proteins which can be chemically altered with hydroxylamine to hydroxamate can be purified with the same method. The principle is applicable to all proteins containing the amino acids Gln and Asn.

The metal ion Fe(III), which chelates the strongest to the hydroxamate group, and Al(III), are preferred, but others like Cu(II), Ni(II), Zn(II), Ce(III), Ca(II) could be used.

BRIEF DESCRIPTION OF THE DRAWINGS

FIG. 2a, b. Principle of the claimed method

EXAMPLE

Figure 1:
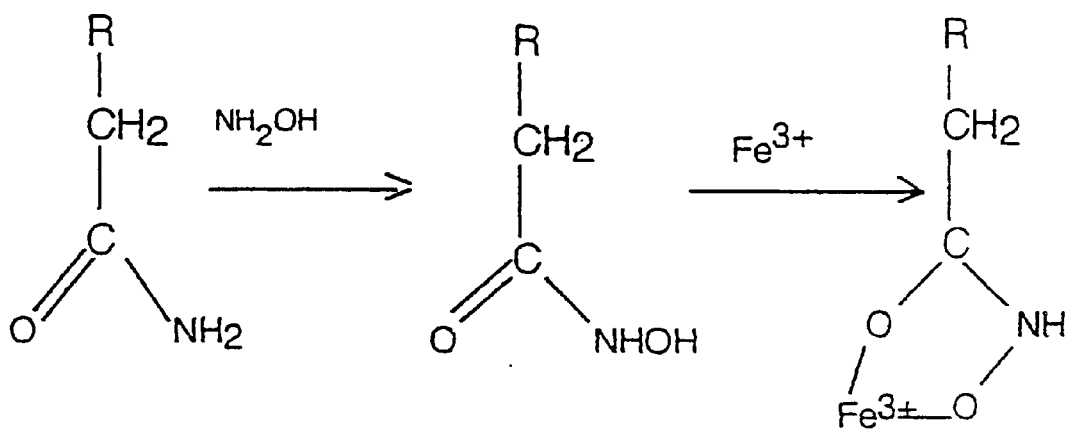
FIG. 1. Amides converted to hydroxamate as bidentate chelate in the presence of Fe(III)

Recombinant human insulin-like growth factor I (rhIGF-I) produced in the *Saccharomyces cerevisiae*, was extensively treated with hydroxylamine in order to convert aspar-agine and glutamine to hydroxamate. The intent was to achieve a significant portion of IGF-I containing hydroxamate, similar to what would occur when the Z-part would be cleaved from Z-IGF-I during hydroxylamine treatment.

rhIGF-I was treated with hydroxylaine cleavage buffer for 24 h instead of the 'normal' incubation time of 5 h. The pure formulated IGF-I (19 ml, 2 mg/ml) was freeze dried and 5 ml cleavage buffer (2M Hydroxylarine, 1.5M NaOH, 2M guanidine hydrochloride (GuHCl), 0.2M 3-(Cyclohexylamino)-2-hydroxy-1-propane sulfonic acid (Capso), 1 mM Ethylenediaminetetraacetic acid (EDTA), 10% ethanol at pH 9.2) was added and the sample incubated at 37° C. for 24 h.

Hydroxylamine buffer was removed after 'cleavage' by Sephadex G25 Fine (1.6×25) that was equilibrated with 0.2M HAc. The sample was freeze-dried and reconstituted with 0.02M TRIS, pH 8.

Pharmacia HR 5/10 was packed with Chelating Sepharose Fast Flow (Code No.:17-0575-01) or TOSOHAAS TSK gel AF-Chelate TOYOPEARL 650 M (Cat. No.:14475). Both gels contain the same chelating ligand (iminodiacetic acid, IDA). The column was packed with 1.1 ml adsorbent chelating Sepharose Fast Flow or TSK gel AF-Chelate TOYOPEARL 650 M (5.8×0.5 mm). Excess of the metal ion Fe(III), that is 50 mM $FeCl_3$, where applied onto the column after equilibrating the column with water (milliQ) and metal ion charge was followed by a water wash until base line was reached or more than 10 column volumes. Then the column was equilibrated with buffer(0.1M Tris pH 8), also more than 10 column volumes or to base line. Sample was applied onto the column and unbound were collected (see FIG. 2a). Adsorbed protein was desorbed with 0.1M EDTA (see FIG. 2b). Both unbound and EDTA desorbed material were desalted on Poros® column and analysed with electrospray mass spectrometry.

A Poros® (11 R/H, 4,6×100 mm, S/N 148) was used to desalt the sample to prepare it for mass spectrometry. After IMAC separation the sample was made 0.05–0.1M in EDTA concentration, before reversed phase separation was performed. A 5 min gradient was used from 0–100% acetonitrile with 0.1% TFA present. Eluted IGF-I was collected and analysed on electrospray mass spectrometry.

Electrospray mass spectrometry and protein assay (Bio-Rad Cat. 500-0006, using BSA as standard) were performed.

Result

Analysis with electrospray mass spectrometry show that hydroxylamine treated IGF-I contain three major peaks of different molecular weight (7647.9, 7663.6 and 7680.0). The lower molecular weight is corresponding to native IGF-I and the higher molecular weight peaks to IGF-I derivatized to one ($\Delta 16$) and two ($\Delta 32$) hydroxamates.

Analysis of the unbound material of IDA-Sepharose charged with Fe(III) at 0.1M Tris pH 8 gave a much reduced content of higher molecular weight ($\Delta 16$ and $\Delta 32$). The IGF-I that was eluted from the same column with EDTA consisted only of higher molecular weight IGF-I.

This clearly shows that IGF-I derivatized to hydroxamate can be removed with IMAC.

The recovery of IGF-I was controlled with a protein assay and was found to be close to 100%.

The same separation and analysis was performed on a TSK gel AF-Chelate TOYOPEARL 650 (also with iminodiacetic acid as a functional group). Analysis with electrospray mass spectrometry gave the same removal of IGF-I containing hydroxamate.

This clearly shows that IGF-I derivatized to hydroxamate can be removed with IMAC.

I claim:

1. Method for providing a purified IGF-I composition by purification of a mixture of hydroxamate derivatized IGF-I and native IGF-I which comprises treating said mixture with immobilized-metal and thereby adsorbing the hydroxamate derivatized IGF-I on the immobilized metal and recovering the native IGF-I.

2. Method according to claim 1 which the metal is selected from the group consisting of iron and aluminum.

3. Method for providing a purified IGF-I composition by separation of native from hydroxamate derivatized IGF-I which comprises adsorbing said hydroxamate derivatized IGF-I on immobilized metal and directly recovering the native IGF-I.

4. Method according to claim 3 in which said IGF-I is rhIGF-I produced from *Saccharomyces cerevisiae.*

5. Method according to claim 1 in which the metal is selected from the group consisting of aluminum, iron, cerium, copper, zinc, calcium and nickel.

6. Method according to claim 1 in which the metal is immobilized on an iminodiacetic acid(IDA)-matrix.

7. Method according to claim 5 in which the metal is immobilized on an iminodiacetic acid(IDA)-matrix.

8. Method according to claim 2 in which the metal is immobilized on an iminodiacetic acid(IDA)-matrix.

9. The method of claim 2 wherein the metal Fe(III) is bound to an iminodiacetic acid (IDA)-matrix.

10. The method of claim 1 wherein said hydroxamate is formed by binding of hydroxylamine to Gln or Asn or both.

11. The method of claim 2 wherein said hydroxamate is formed by binding of hydroxylamine to Gln or Asn or both.

12. The method of claim 3 wherein said hydroxamate is formed by binding of hydroxylamine is bound to Gln or Asn or both.

13. The method of claim 4 wherein said hydroxamate is formed by binding of hydroxlamine is bound to Gln or Asn or both.

14. Method according to claim 1 wherein said IGF-I is rhIGF-I produced from *Saccharomyces cerevisiae.*

15. Method according to claim 9 wherein said IGF-I is rhIGF-I produced from *Saccharomyces cerevisiae.*

* * * * *